United States Patent
Laub

(10) Patent No.: US 10,857,100 B2
(45) Date of Patent: *Dec. 8, 2020

(54) METHODS AND COMPOSITIONS FOR ADMINISTERING AN ACTIVE AGENT TO THE PLEURA OF A PATIENT

(71) Applicant: TDL Innovations LLC, Princeton, NJ (US)

(72) Inventor: Glenn W. Laub, Princeton, NJ (US)

(73) Assignee: TDL Innovations LLC, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/172,171

(22) Filed: Oct. 26, 2018

(65) Prior Publication Data

US 2020/0129430 A1     Apr. 30, 2020

Related U.S. Application Data

(63) Continuation of application No. 14/674,047, filed on Mar. 31, 2015, now Pat. No. 10,111,834.

(60) Provisional application No. 61/973,703, filed on Apr. 1, 2014.

(51) Int. Cl.
| | |
|---|---|
| A61K 33/18 | (2006.01) |
| A61K 47/36 | (2006.01) |
| A61K 9/12 | (2006.01) |
| A61K 9/00 | (2006.01) |
| A61K 31/79 | (2006.01) |
| A61K 38/14 | (2006.01) |
| A61K 47/10 | (2017.01) |
| A61K 31/65 | (2006.01) |
| A61K 47/42 | (2017.01) |

(52) U.S. Cl.
CPC .............. *A61K 9/122* (2013.01); *A61K 33/18* (2013.01); *A61K 47/36* (2013.01); *A61K 9/0019* (2013.01); *A61K 31/65* (2013.01); *A61K 31/79* (2013.01); *A61K 38/14* (2013.01); *A61K 47/10* (2013.01); *A61K 47/42* (2013.01)

(58) Field of Classification Search
CPC ......... A61K 33/18; A61K 47/36; A61K 9/122
See application file for complete search history.

(56) References Cited

U.S. PATENT DOCUMENTS

| | | | |
|---|---|---|---|
| 2,190,688 | A | 2/1940 | Snelling |
| 2,569,683 | A | 10/1951 | Lindsay |
| 5,054,688 | A | 10/1991 | Grindley |
| 6,042,089 | A | 3/2000 | Klein |
| 6,103,695 | A | 8/2000 | Lane et al. |
| 7,100,799 | B2 | 9/2006 | Gruenewald et al. |
| 8,198,365 | B2 | 6/2012 | Ingenito et al. |
| 8,445,589 | B2 | 5/2013 | Ingenito et al. |
| 8,501,230 | B2 | 8/2013 | Alur et al. |
| 8,691,278 | B2 | 4/2014 | Alur et al. |
| 10,111,834 | B2 * | 10/2018 | Laub |
| 2003/0152522 | A1 | 8/2003 | Miller et al. |
| 2004/0151774 | A1 | 8/2004 | Pauletti et al. |
| 2006/0009801 | A1 | 1/2006 | McGurk et al. |
| 2008/0261884 | A1 | 10/2008 | Tsai et al. |
| 2008/0281433 | A1 | 11/2008 | Chang et al. |
| 2010/0075001 | A1 | 3/2010 | Succar |
| 2013/0028181 | A1 * | 1/2013 | Rosen |
| 2013/0046275 | A1 | 2/2013 | Holzer et al. |
| 2013/0131166 | A1 | 5/2013 | Alur et al. |
| 2013/0150883 | A1 | 6/2013 | Fette et al. |
| 2015/0272883 | A1 | 10/2015 | Laub |
| 2018/0169012 | A1 | 6/2018 | Laub |

FOREIGN PATENT DOCUMENTS

| | | |
|---|---|---|
| WO | 2009073658 A1 | 6/2009 |
| WO | 2013011504 A1 | 1/2013 |
| WO | 2015153540 A2 | 10/2015 |

OTHER PUBLICATIONS

Mondal et al., "Evaluation of TRI-726 as a Drug Delivery Matrix," Drug Development and Industrial Pharmacy (2011); pp. 1-7.
Falkenstern-GE et al., "Sever Emphysema Treated by Endoscoic Bronchial Volume Reduction with Lung Sealant (AeriSeal)," Hindawi Publishing Corp., Case Reports in Pulmonology, vol. 2013, Aricle ID 361391, 4 pages.
Oda et al., "Experimental Use of an Elastomeric Surgical Sealant for Arterial Hemostasis and its Long-Term Tissue Response," Interactive Cardiovascular and Thoracic Surgery (2010); 10:258-261.
Albanese et al., "Pharmacology of Sclerotherapy," Seminars in Interventional Radiology, (2010); 27(4):391-399.
Shiels, William, E., "Presentation re: New Concepts in Percutaneous MSK Treatment," ISSVA 2012, Malmo, Sweden, 37 pages.
Vaz et al.,"Pleurodesis: Technique and Indications," J. Bras Pleumol., (2006); 32(4):347-56.

(Continued)

*Primary Examiner* — Alma Pipic
(74) *Attorney, Agent, or Firm* — Fox Rothschild LLP

(57) ABSTRACT

A method for administering an active agent to a pleura of a patient includes preparing a composition including a foamable liquid and the active agent, incorporating a gas into the foamable liquid to create a foam containing the active agent, introducing the foam into a pleural cavity of the patient defined by the pleura, and contacting the pleura with the foam. A method of pleurodesis includes introducing a composition into a pleural cavity defined by pleurae of a patient, the composition including a foamable liquid and an active agent capable of causing inflammation and/or adhesion of the pleurae. A composition for treating a pleura of a patient includes a liquid component including a biocompatible composition having a viscosity which increases in response to an increase in temperature, and an active agent capable of causing inflammation and/or adhesion of the pleura.

14 Claims, 1 Drawing Sheet

(56) References Cited

OTHER PUBLICATIONS

Jin Pu-le et al., "Localization of the bronchial air leakage in pneumothorax by injection of human albumin foam," Chinese Journal of Tuberculosis and Respiratory Diseases (May 2011); 34(5):Abstract.
European Extended Search Report for European Patent Application No. 15774160.4 dated Oct. 25, 2017.
Definition of Pleurodesis (Accessed on Nov. 8, 2017, 1 page, https://www.medicinenet.com/script/main/art.asp?articlekey=20053).
Kennedy et al., "Pleurodesis Using Talc Slurry," Chest (Aug. 1994) 106(2):342-346.
International Search Report and Written Opinion of the International Searching Authority for International Application No. PCT/US2015/023468 dated Jul. 7, 2015.

* cited by examiner

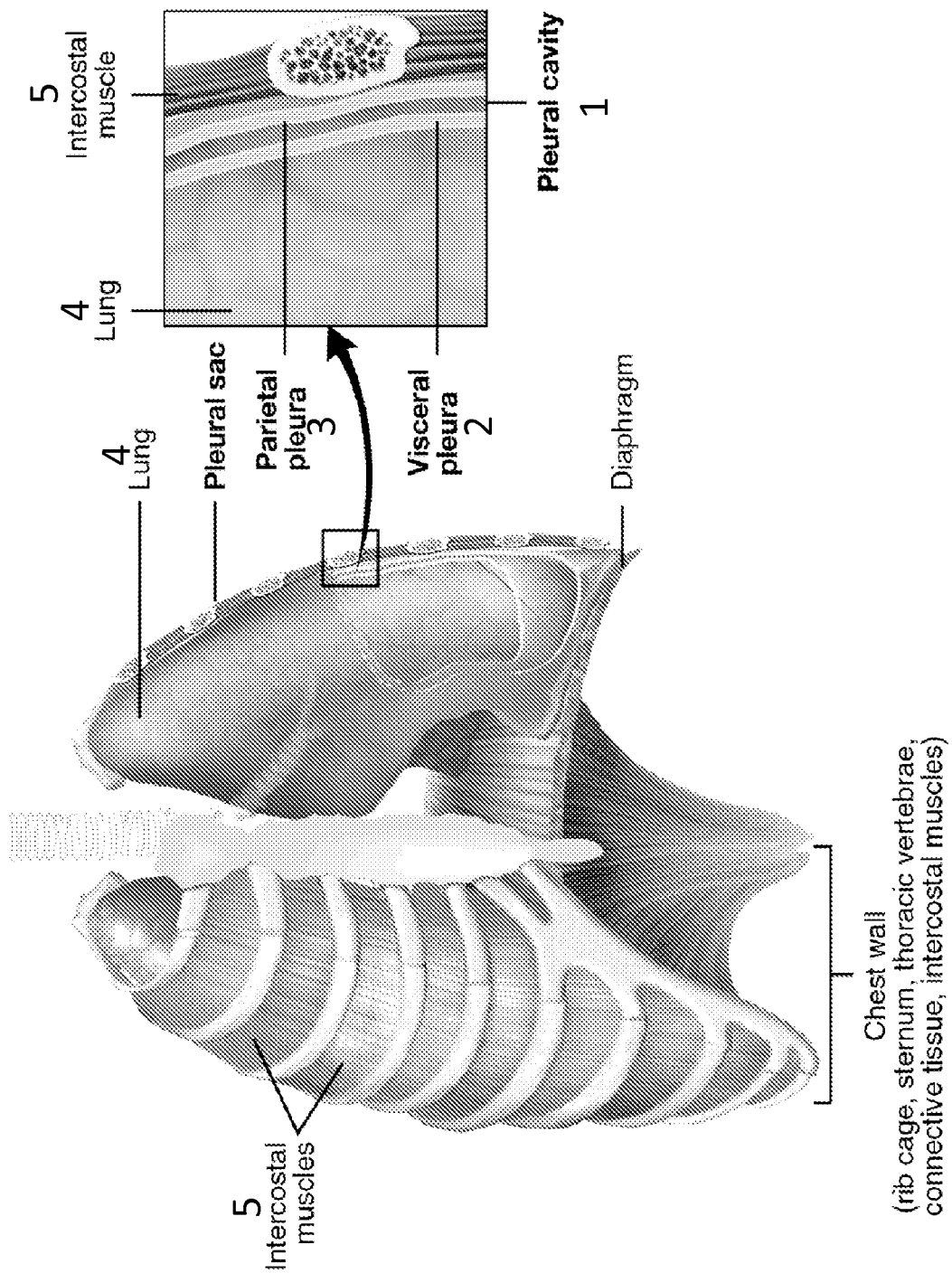

METHODS AND COMPOSITIONS FOR ADMINISTERING AN ACTIVE AGENT TO THE PLEURA OF A PATIENT

CROSS-REFERENCE TO RELATED APPLICATIONS

This application is a continuation of U.S. application Ser. No. 14/674,047, filed Mar. 31, 2015, which claims the benefit of U.S. Provisional Patent Application No. 61/973,703, filed Apr. 1, 2014, which is incorporated herein by reference in its entirety.

FIELD OF THE INVENTION

The present invention, according to some embodiments, relates to methods and compositions for administering one or more active agents to a patient. More particularly, the present invention in some embodiments relates to methods and compositions for administering one or more active agents to the pleura of a patient. In some embodiments, the present invention relates to methods and compositions that are useful for pleurodesis. In some embodiments, the present invention relates to methods and compositions that are useful for treating pleural effusions, particularly malignant pleural effusions.

BACKGROUND OF THE INVENTION

The pleura is a membrane which surrounds the lungs and has a two-layer structure including an outer or parietal pleura that is normally attached to the chest wall and an inner or visceral pleura that covers the lungs and adjoining structures. The space between the inner and outer pleurae is referred to as the pleural cavity, pleural space, or intrapleural space.

For ease of illustration, reference is made to the appended FIGURE which is a simplified diagram showing pleural cavity 1, visceral pleura 2, and parietal pleura 3 in relation to lungs 4 and intercostal muscle 5 of an example human (adapted from *OpenStax College. "Anatomy & Physiology." Connexions.* Jun. 19, 2013.).

In healthy patients a small amount of pleural fluid, typically a few milliliters, is usually present in the pleural cavity. This fluid is normally produced and reabsorbed continuously such that no considerable accumulation of fluid occurs in the pleural cavity. Certain pathological conditions can lead to an increase in pleural fluid production and/or a decrease in fluid absorption, resulting in a significant accumulation of excess fluid in the pleural cavity. Blood, pus, and/or other bodily fluids may also accumulate in the pleural cavity under certain conditions. This pathologic collection of fluid in the pleural cavity is known as a pleural effusion.

Pleural effusions may be caused by a number of medical conditions including, for example, congestive heart failure, infections, pneumonia, pulmonary embolism, and cancers. Malignant pleural effusions refer to a type of pleural effusion in which the excess accumulation of fluid in the pleural cavity is specifically caused by cancer. Malignant pleural effusions may be caused, for example, by lung cancer, breast cancer, lymphoma, and pleural mesothelioma.

Pleural effusions, including malignant pleural effusions, can impair normal breathing by significantly limiting the expansion of the lungs. In some cases the excess fluid accumulation in the pleural cavity compresses the lungs resulting in breathlessness and/or lung collapse. For some patients, treating the underlying cause of the pleural effusions (e.g., treating the cancer causing a malignant pleural effusion) may be sufficient to mitigate the pleural effusion. Other treatments for pleural effusions include aspiration of the excess fluid or insertion of a chest tube (e.g., thoracic cather, tube thoracostomy, or intercostal drain) into the pleural cavity of the patient to drain the excess fluid. While aspiration or drainage may provide immediate relief for the patient, fluid accumulation and symptoms may reappear such that repeated aspirations or continuous drainage is required.

Pleurodesis, a procedure in which the pleural cavity is treated in an attempt to reduce or eliminate the potential pleural space, may be used to treat patients suffering from recurrent pleural effusions by reducing or obliterating the potential space in which fluid may accumulate. Pleurodesis typically involves fusing together the outer and inner pleurae and may be carried out using surgical and/or chemical means. Examples of typical procedures for pleurodesis are described in Vaz et al., *"Pleurodesis: technique and indications," J Bras Pneumol.* 2006; 32(4):347-56, which is incorporated herein by reference in its entirety. Fusion of the inner and outer pleurae may be accomplished, for example, by triggering fibrosis or the formation scar tissue between the inner and outer pleurae to cause the pleural layers to fuse together. Surgical pleurodesis may include, for example, mechanically irritating the pleura and causing the layers of the pleura to scar together. This procedure can be performed, for instance, by scraping the outer pleura with a rough pad (e.g., via thoracotomy). In chemical pleurodesis, a chemical agent which causes inflammation for inducing fibrosis between the inner and outer pleura, for example, may be introduced into the pleural cavity (e.g., via a catheter or chest drain) to fuse the inner and outer pleurae together. Certain chemical agents and procedures that may be suitable for pleurodesis are described in U.S. Pat. No. 6,103,695, which is incorporated herein by reference in its entirety.

Chemical pleurodesis is sometimes preferred over surgical pleurodesis since chemical pleurodesis may be less invasive. However, treatment success can be suboptimal as substantial or adequate reduction of the pleural cavity can be difficult to achieve in some circumstances when the chemical agent is not effectively distributed throughout the pleural cavity of the patient. When portions of the pleura are not sufficiently exposed to the chemical agent, incomplete fusion of the pleural layers may occur. For example, because the chemical agent used in chemical pleurodesis is typically introduced in a liquid or slurry, the chemical agent may collect at certain locations in the pleural cavity due to gravity, possibly resulting in an uneven distribution of the chemical agent. In some cases the chemical agent may not maintain contact with portions of the pleura for a sufficient amount of time to trigger fibrosis because, for example, the liquid or slurry drains to lower regions of the pleural cavity.

SUMMARY OF THE INVENTION

The present invention, according to some embodiments, relates to methods and compositions for administering one or more active agents to a patient. More particularly, the present invention in some embodiments relates to methods and compositions for administering one or more active agents to the pleura of a patient. In some embodiments, the present invention relates to methods and compositions that are useful for pleurodesis. In some embodiments, the present invention relates to methods and compositions that are useful for treating pleural effusions, for example, malignant pleural effusions. In further embodiments, methods and compositions of the present invention may be useful for treating infections or bleeding in the pleural cavity, pneumothorax, and/or hemothorax.

Methods according to certain embodiments of the present inventions include administering a composition comprising or consisting of a foamable liquid to a pleura of a patient. In some embodiments, a method for administering an active agent to a pleura of a patient includes preparing a composition comprising a foamable liquid and the active agent, incorporating a gas into the foamable liquid to create a foam containing the active agent, and introducing the foam into a pleural cavity of the patient defined by the pleura; and contacting the pleura with the foam. As used herein, the term foamable liquid refers to a liquid having the ability to form a foam. In certain embodiments, the foamable liquid by itself is an active agent.

In further embodiments, a method according to the present invention includes introducing a composition into a pleural cavity defined by pleurae of a patient, the composition comprising a foamable liquid and an active agent capable of causing inflammation and/or adhesion of the pleurae, contacting the pleurae with the composition for an amount of time sufficient to initiate inflammation and/or adhesion of the pleurae by the active agent, and allowing the pleurae to seal together to reduce a volume of the pleural cavity. According to some of these embodiments, the foamable liquid is mixed with a gas to form a foam prior to introducing the composition into the pleural cavity such that contacting the pleurae with the composition includes contacting the pleurae with the foam. In other embodiments, the foamable liquid is mixed with gas during or after the composition is introduced into the pleural cavity.

In some embodiments, the foam has a volume of about 10 to about 1000 times greater than the volume of the foamable liquid. In some embodiments, the foam comprises bubbles of the gas having a size range of about 1 mm to about 10 mm in diameter. In some embodiments, the gas may include air, carbon dioxide, oxygen, hydrogen, helium, argon or combinations thereof.

Some methods of the present invention further include removing at least a portion of the foam from the pleural cavity after contacting the pleurae with the foam. In some embodiments, at least a portion of the gas is allowed to separate from the foam after contacting the pleurae with the foam. For example, the foam may be allowed to collapse or dissipate within the pleural cavity of the patient. After the foam has collapsed or dissipated, at least a portion of the residual liquid or gas may be absorbed by the patient's body or drained from the pleural cavity according to some embodiments. In further embodiments, removing at least a portion of the foam from the pleural cavity includes one or more of aspirating, draining, and intubation of the pleural cavity. In other embodiments, at least a portion of the foam may be removed from the pleural cavity by allowing the foam to be absorbed by the patient's body.

In some embodiments, the foamable liquid may include, for example, liquid solutions, slurries, suspensions, or colloidal solutions. In some embodiments, the foamable liquid includes a gel or a composition configured to form a gel (e.g., a hydrogel). In other embodiments, the foamable liquid does not include a gel (e.g., a hydrogel) or a cross-linked polymer network. In some embodiments, the foamable liquid is an aqueous solution. In some embodiments, the foamable liquid may further include one or more surfactants and/or proteins that are selected to modify the stability of the foam formed when the foamable liquid is admixed with a gas. In some embodiments, for example, the foamable liquid includes albumin (e.g., human serum albumin), which may be present in the foamable liquid at a concentration of about 5% to about 25% by weight of the foamable liquid.

The active agent used in embodiments of the present invention may be dissolved, dispersed, suspended, or carried by the foamable liquid. In some embodiments, the active agent is dissolved, dispersed, suspended, or carried by the foamable liquid prior to foaming the foamable liquid. The active agent may be present in an amount of about 0.1% to about 50% by weight of the foamable liquid according to some embodiments. In some embodiments, the foamable liquid itself is an active agent, for example, suitable for use in chemical pleurodesis.

In some embodiments, the active agent is a chemical agent useful for chemical pleurodesis. In some embodiments, the active agent includes a sclerosing agent. In some embodiments, the active agent is selected to cause irritation, inflammation, fibrosis, and/or scarring of the patient's pleura when introduced into the pleural cavity of the patient. In some embodiments, the active agent includes one or more agents selected from the following: doxycycline, bleomycin, tetracycline, povidone iodine, talc, silica (e.g., fumed silica), and quinacrine. In some embodiments, the active agents include a chemotherapy agent, an antibiotic, or combinations thereof. In some embodiments, the active agent is an adhesive, for example, an adhesive adapted to adhere the pleural layers together. In some embodiments, the adhesive comprises one or more agents selected from the group consisting of: collagen-based adhesives, fibrin-based adhesives, cyanoacrylates, fibrin sealants, gelatin-resorcin-aldehydes, protein-aldehyde systems, polysaccharide-based adhesives, mussel adhesive proteins, and biomimetic glues.

In further embodiments, the present invention includes a composition for administering an active agent to a pleura of a patient, the composition including a liquid component comprising a biocompatible composition having a viscosity which increases in response to an increase in temperature, and an active agent dissolved, dispersed, or suspended in the liquid component, the active agent being capable of causing inflammation and/or adhesion of the pleurae. In some of these embodiments, the viscosity of the biocompatible composition is configured to increase at least three times when the temperature of the biocompatible composition increases from about 25° C. to about 37° C. In some of these embodiments, the viscosity of the biocompatible composition is configured to increase at least ten times when the temperature of the biocompatible composition increases from about 25° C. to about 37° C. In some of these embodiments, the viscosity of the biocompatible composition is configured to increase at least a hundred times when the temperature of the biocompatible composition increases from about 25° C. to about 37° C. In some embodiments, the biocompatible composition is selected to have a viscosity at about room temperature that is less than 500,000 cP, less than 400,000 cP, less than 300,000 cP, less than 200,000 cP, less than 100,000, less than 50,000 cP, less than 10,000 cP, less than 5,000 cP, less than 1,000 cP, less than 500 cP, less than 100 cP, less than 50 cP, less than 10 cP, less than 5 cP, or less than 1 cP. In some embodiments, the biocompatible composition is selected to have a viscosity at about human body temperature that is at least 10,000 cP, at least 50,000 cP, at least 100,000 cP, at least 200,000 cP, at least 300,000, at least 400,000 cP, at least 500,000 cP, at least 600,000 cP, at least 700,000 cP, at least 800,000 cP, at least 900,000 cP, or at least 1,000,000 cP. In some embodiments, the biocompatible composition is configured to form a gel after administration to the patient. In some embodiments, the biocompatible composition includes one or more copolymers of ethylene oxide and propylene oxide. In further embodiments, the biocompatible composition includes one or more poloxamers, xanthan gum, and water. The liquid component may be a foamable liquid, according to some embodiments. In some embodiments, the composition further includes a gas having a volume greater than a volume of the liquid component. In other embodiments, the liquid component is not foamed before, during, and/or after administration to the patient. The active agent may be selected from the group consisting of selected from the group consisting of: doxycycline, bleomycin, tetracycline, povidone iodine, talc, silica, and quinacrine according to some embodiments. In other embodiments, the active agent may be an adhesive, for example, selected from the group consisting of collagen-based adhesives, fibrin-based adhesives, cyanoacrylates, fibrin sealants, gelatin-resorcin-aldehydes, protein-aldehyde systems, polysaccharide-based adhesives, mussel adhesive proteins, and biomimetic glues.

BRIEF DESCRIPTION OF THE DRAWING

The FIGURE is an illustration showing the parietal and visceral pleurae of the lungs of a human.

DETAILED DESCRIPTION

The present subject matter will now be described more fully hereinafter in which representative embodiments are described. The present subject matter can, however, be embodied in different forms and should not be construed as limited to the embodiments set forth herein. Rather, these embodiments are provided to describe and enable one of skill in the art. While particular embodiments described herein are illustrative of methods and compositions useful for pleurodesis, for example, in the treatment of pleural effusions, the present invention is not intended to be limited to these uses. Indeed, other treatments may benefit from the advantages provided by the methods and compositions described herein.

The present invention, according to certain embodiments, generally includes methods and compositions for administering one or more active agents to a patient. In some embodiments, the methods and compositions of the present invention are particularly adapted for administering one or more active agents to the pleura of a patient. In some embodiments, for example, the methods and compositions described herein are useful for treating pleural effusions (e.g., malignant pleural effusions). In particular, certain preferred embodiments of the invention relate to methods and compositions that are useful for pleurodesis. Such methods and compositions, for example, may be used to reduce or obliterate the pleural cavity of a patient to prevent fluid buildup in the pleural cavity.

Some embodiments of the present invention relate to preparing a composition including one or more active agents and introducing the composition into a pleural cavity of the patient. In some embodiments, the compositions of the present invention include flowable compositions containing one or more active agents. In some embodiments, the compositions of the present invention are adapted to be introduced into the pleural cavity of a patient, for example, via a catheter or a chest drain. In some embodiments, the compositions may be sprayed, injected or pumped into the pleural cavity of the patient.

In some embodiments, the compositions of the present invention may include homogeneous mixtures or heterogeneous mixtures. In some embodiments, the compositions may include one or more liquid components which may be used to dissolve, suspend, disperse, or carry the one or more active agents. In some embodiments, the one or more liquid components are active agents. The liquid component may, for example, include liquid solutions, slurries, suspensions, or colloidal solutions. Moreover, the liquid component in some embodiments may include aqueous or non-aqueous liquids. In some embodiments, the liquid component is configured to undergo an increase in viscosity during and/or after introduction into the body of a patient (e.g., into the pleural cavity). In some embodiments, the liquid component forms a mucoadhesive configured to adhere to the pleura of the patient. In some embodiments, the liquid component is or includes a gel, or a composition which is configured to form a gel (e.g., a hydrogel). In some embodiments, the liquid component is configured to form a gel after introduction into the body of a patient (e.g., into the pleural cavity). In yet other embodiments, the liquid component is not or does not form a gel (e.g., a hydrogel). In further embodiments, the compositions of the present invention may also include one or more components in a gaseous state. In some embodiments, the compositions include a gas or mixture of gases which may be admixed with the liquid component.

Compositions according to certain embodiments of the present invention include a foamable liquid as the liquid component. As used herein, the term foamable liquid refers to a liquid having the ability to form a foam. In some embodiments, the foamable liquid is configured to form a foam when the foamable liquid is admixed with a gas. As described herein, the foamable liquid may include, for example, liquid solutions, slurries, suspensions, or colloidal solutions. In other embodiments, the foamable liquid includes a gel or a composition which forms a gel (e.g., a hydrogel). In other embodiments, the foamable liquid is not or does not form a gel (e.g., a hydrogel) or a cross-linked polymer network. In some embodiments, the foamable liquid includes water. In some embodiments, the foamable liquid includes an aqueous solution, preferably an aqueous solution that can be absorbed by the patient's body without substantial adverse (e.g., toxic) effects. In some embodiments, the aqueous solution includes a saline solution. In some embodiments, the foamable liquid includes one or more of lipids, phospholipids, neutral lipids, and alcohols. In some embodiments, the liquid component is admixed with a gas to form a foam prior to administration to the patient, as will be described further herein. In other embodiments, the liquid component is configured to be administered to a patient in an unfoamed state and foamed within the patient's body (e.g., within the pleural cavity). In yet other embodiments, the liquid component is not foamed.

Gases useful in the foamed compositions of the present invention preferably include gases that can be readily instilled into the body of the patient without substantial adverse (e.g., toxic) effects. In some embodiments, the gas is selected from the group consisting of air, carbon dioxide, oxygen, hydrogen, helium, argon, and mixtures thereof. Preferably, according to some embodiments, the gas is not pure nitrogen. In other embodiments, the gas includes one or more organic compounds. In some embodiments, the gas includes one or more hydrocarbons, for example, n-butane, n-pentane, or other saturated low boiling point aliphatic hydrocarbons. In further embodiments, the gas may include one or more fluorocarbons and/or hydrofluorocarbons. Other aerosol spray propellants known in the art which do not have substantial adverse effects may also be used according to some embodiments. The gas in some embodiments includes vapors that may be, for example, produced from the evaporation or sublimation of a liquid or solid substance. In some embodiments, for example, the gas includes a volatile compound mixed with the foamable liquid and which causes the foamable liquid to foam as the volatile compound vaporizes. In some embodiments, the gas is generated from a chemical reaction, for example, an acid-base reaction. In some such embodiments, the foamable liquid may be or include a chemical reactant that reacts to produce a gas.

In further embodiments, the liquid component includes one or more surfactants. The one or more surfactants may include a biocompatible foaming agent selected to modify the stability of the foam formed when the foamable liquid is admixed with a gas. In some embodiments, the surfactants may further function as a sclerosing agent. In some embodiments, one or more surfactants includes sodium tetradecyl sulfate. Other surfactants that may be useful according to certain embodiments of the present invention include phospholipids, neutral lipids, hydrophobic surfactants, biocompatible soaps or detergents, and combinations thereof.

In some embodiments, the liquid component includes one or more polypeptides. In some embodiments, the liquid component includes one or more proteins. In some embodiments, the one or more proteins include an albumin (e.g., human serum albumin). Other proteins that may be used in the liquid component according to certain embodiments include surfactant associated proteins, for example, surfactant associated proteins B or C. In some embodiments, the one or more proteins includes only albumin. In other embodiments, the one or more proteins includes only surfactant associated proteins. In some embodiments, the one or more proteins includes a combination of albumin and a surfactant associated protein. In some embodiments, the albumin and/or other proteins included in the liquid component enhances the liquid component's ability to form a foam when the liquid component is admixed with a gas. In some embodiments, the one or more proteins (e.g., albumin) is present in the liquid component in an amount that is at least 0.5% by weight of the liquid component. In some embodiments, the one or more proteins (e.g., albumin) is present in the liquid component in an amount that is at least 1% by weight of the liquid component. In some embodiments, the one or more proteins (e.g., albumin) is present in the liquid component in an amount that is at least 5% by weight of the liquid component. In some embodiments, the one or more proteins (e.g., albumin) is present in the liquid component in an amount that is at least 10% by weight of the liquid component. In some embodiments, the one or more proteins (e.g., albumin) is present in the liquid component in an amount that is at least 15% by weight of the liquid component. In some embodiments, the one or more proteins (e.g., albumin) is present in the liquid component in an amount that is at least 20% by weight of the liquid component. In some embodiments, the one or more proteins (e.g., albumin) is present in the liquid component in an amount that is at least 25% by weight of the liquid component. In some embodiments, the one or more proteins (e.g., albumin) is present in the liquid component in an amount that is at least 30% by weight of the liquid component. In some embodiments, the one or more proteins (e.g., albumin) is present in the liquid component in an amount from about 1% to about 10% by weight of the liquid component. In some embodiments, the one or more proteins (e.g., albumin) is present in the liquid component in an amount from about 1% to about 20% by weight of the liquid component. In some embodiments, the one or more proteins (e.g., albumin) is present in the liquid component in an amount from about 1% to about 30% by weight of the liquid component. In some embodiments, the one or more proteins (e.g., albumin) is present in the liquid component in an amount from about 1% to about 40% by weight of the liquid component. In some embodiments, the one or more proteins (e.g., albumin) is present in the liquid component in an amount from about 1% to about 50% by weight of the liquid component. In some embodiments, the one or more proteins (e.g., albumin) is present in the liquid component in an amount from about 5% to about 25% by weight of the liquid component. In some embodiments, the one or more proteins (e.g., albumin) is present in the liquid component in an amount from about 10% to about 20% by weight of the liquid component. In some embodiments, the one or more proteins (e.g., albumin) is present in the liquid component in an amount no more than 50% by weight of the liquid component.

In some embodiments, a liquid component includes or consists of a biocompatible composition having a viscosity which increases during or after introduction into the body of the patient. In some embodiments, a liquid component includes or consists of a biocompatible composition having a viscosity which increases in response to an increase in temperature (e.g., from about room temperature to about human body temperature). In some embodiments, the liquid component includes a gel or a composition which forms a gel. In some embodiments, where the liquid component includes a gel or a composition which forms a gel, the liquid component may or may not also include one or more proteins (e.g., albumin or surfactant associated proteins), and may or may not include one or more surfactants as described above. In preferred embodiments, the gel or composition which forms a gel exhibits mucoadhesive properties. In some embodiments, the gel or composition which forms a gel exhibits mucoadhesive properties when or after being introduced into the pleural cavity of a patient. In some embodiments, the gel or composition which forms a gel is configured to adhere to the inner and outer pleurae of the patient after introduction into the pleural cavity. In some embodiments, the gel or composition which forms a gel includes or consists only of a biocompatible, biodegradable hydrogel. In some embodiments, the gel or composition which forms a gel includes one or more materials configured to form a gel during and/or after introduction into the patient (e.g., into the pleural cavity). In some embodiments, the gel or composition which forms a gel is configured to increase in viscosity after introduction into the patient such that, for example, the gel or composition which forms a gel can be introduced into the patient as a liquid and/or a foam. In some embodiments the gel or composition which forms a gel exhibits in situ reverse-thermal gelling.

In some embodiments, the liquid component includes or consists of a gel, or a composition which forms a gel, that is substantially liquid (low viscosity) at about room temperature (e.g., about 20° C. to about 25° C.). In some embodiments, the viscosity of the gel or composition which forms a gel is less than 800,000 centipoise (cP) at about room temperature. In some embodiments, the viscosity of the gel or composition which forms a gel is less than 750,000 cP at about room temperature. In some embodiments, the viscosity of the gel or composition which forms a gel is less than 700,000 cP at about room temperature. In some embodiments, the viscosity of the gel or composition which forms a gel is less than 650,000 cP at about room temperature. In some embodiments, the viscosity of the gel or composition which forms a gel is less than 600,000 cP at about room temperature. In some embodiments, the viscosity of the gel or composition which forms a gel is less than 550,000 cP at about room temperature. In some embodiments, the viscosity of the gel or composition which forms a gel is less than 500,000 cP at about room temperature. In some embodiments, the viscosity of the gel or composition which forms a gel is less than 450,000 cP at about room temperature. In some embodiments, the viscosity of the gel or composition which forms a gel is less than 400,000 cP at about room temperature. In some embodiments, the viscosity of the gel or composition which forms a gel is less than 350,000 cP at about room temperature. In some embodiments, the viscosity of the gel or composition which forms a gel is less than 300,000 cP at about room temperature. In some embodiments, the viscosity of the gel or composition which forms a gel is less than 250,000 cP at about room temperature. In some embodiments, the viscosity of the gel or composition which forms a gel is less than 200,000 cP at about room temperature. In some embodiments, the viscosity of the gel or composition which forms a gel is less than 150,000 cP at about room temperature. In some embodiments, the viscosity of the gel or composition which forms a gel is less than 100,000 cP at about room temperature. In some embodiments, the viscosity of the gel or composition which forms a gel is less than 90,000 cP at about room temperature. In some embodiments, the viscosity of the gel or composition which forms a gel is less than 80,000 cP at about room temperature. In some embodiments, the viscosity of the gel or composition which forms a gel is less than 70,000 cP at about room temperature. In some embodiments, the viscosity of the gel or composition which forms a gel is less than 60,000 cP at about room temperature. In some embodiments, the viscosity of the gel or composition which forms a gel is less than 50,000 cP at about room temperature. In some embodiments, the viscosity of the gel or composition which forms a gel is less than 40,000 cP at about room temperature. In some embodiments, the viscosity of the gel or composition which forms a gel is less than 30,000 cP at about room temperature. In some embodiments, the viscosity of the gel or composition which forms a gel is less than 20,000 cP at about room temperature. In some embodiments, the viscosity of the gel or composition which forms a gel is less than 10,000 cP at about room temperature. In some embodiments, the viscosity of the gel or composition which forms a gel is less than 9,000 cP at about room temperature. In some embodiments, the viscosity of the gel or composition which forms a gel is less than 8,000 cP at about room temperature. In some embodiments, the viscosity of the gel or composition which forms a gel is less than 7,000 cP at about room temperature. In some embodiments, the viscosity of the gel or composition which forms a gel is less than 6,000 cP at about room temperature. In some embodiments, the viscosity of the gel or composition which forms a gel is less than 5,000 cP at about room temperature. In some embodiments, the viscosity of the gel or composition which forms a gel is less than 4,000 cP at about room temperature. In some embodiments, the viscosity of the gel or composition which forms a gel is less than 3,000 cP at about room temperature. In some embodiments, the viscosity of the gel or composition which forms a gel is less than 2,000 cP at about room temperature. In some embodiments, the viscosity of the gel or composition which forms a gel is less than 1,000 cP at about room temperature. In some embodiments, the viscosity of the gel or composition which forms a gel is less than 900 cP at about room temperature. In some embodiments, the viscosity of the gel or composition which forms a gel is less than 800 cP at about room temperature. In some embodiments, the viscosity of the gel or composition which forms a gel is less than 700 cP at about room temperature.

In some embodiments, the viscosity of the gel or composition which forms a gel is less than 600 cP at about room temperature. In some embodiments, the viscosity of the gel or composition which forms a gel is less than 500 cP at about room temperature. In some embodiments, the viscosity of the gel or composition which forms a gel is less than 400 cP at about room temperature. In some embodiments, the viscosity of the gel or composition which forms a gel is less than 300 cP at about room temperature. In some embodiments, the viscosity of the gel or composition which forms a gel is less than 200 cP at about room temperature. In some embodiments, the viscosity of the gel or composition which forms a gel is less than 100 cP at about room temperature. In some embodiments, the viscosity of the gel or composition which forms a gel is less than 90 cP at about room temperature. In some embodiments, the viscosity of the gel or composition which forms a gel is less than 80 cP at about room temperature. In some embodiments, the viscosity of the gel or composition which forms a gel is less than 70 cP at about room temperature. In some embodiments, the viscosity of the gel or composition which forms a gel is less than 60 cP at about room temperature. In some embodiments, the viscosity of the gel or composition which forms a gel is less than 50 cP at about room temperature. In some embodiments, the viscosity of the gel or composition which forms a gel is less than 40 cP at about room temperature. In some embodiments, the viscosity of the gel or composition which forms a gel is less than 30 cP at about room temperature. In some embodiments, the viscosity of the gel or composition which forms a gel is less than 20 cP at about room temperature. In some embodiments, the viscosity of the gel or composition which forms a gel is less than 10 cP at about room temperature. In some embodiments, the viscosity of the gel or composition which forms a gel is less than 9 cP at about room temperature. In some embodiments, the viscosity of the gel or composition which forms a gel is less than 8 cP at about room temperature. In some embodiments, the viscosity of the gel or composition which forms a gel is less than 7 cP at about room temperature. In some embodiments, the viscosity of the gel or composition which forms a gel is less than 6 cP at about room temperature. In some embodiments, the viscosity of the gel or composition which forms a gel is less than 5 cP at about room temperature. In some embodiments, the viscosity of the gel or composition which forms a gel is less than 4 cP at about room temperature. In some embodiments, the viscosity of the gel or composition which forms a gel is less than 3 cP at about room temperature. In some embodiments, the viscosity of the gel or composition which forms a gel is less than 2 cP at about room temperature. In some embodiments, the viscosity of the gel or composition which forms a gel is less than 1 cP at about room temperature. In some embodiments, the viscosity of the gel or composition which forms a gel is less than 0.9 cP at about room temperature. In some embodiments, the viscosity of the gel or composition which forms a gel is less than 0.8 cP at about room temperature. In some embodiments, the viscosity of the gel or composition which forms a gel is less than 0.7 cP at about room temperature. In some embodiments, the viscosity of the gel or composition which forms a gel is less than 0.6 cP at about room temperature. In some embodiments, the viscosity of the gel or composition which forms a gel is less than 0.5 cP at about room temperature. In some embodiments, the viscosity of the gel or composition which forms a gel is less than 0.4 cP at about room temperature. In some embodiments, the viscosity of the gel or composition which forms a gel is less than 0.3 cP at about room temperature. In some embodiments, the viscosity of the gel or composition which forms a gel is less than 0.2 cP at about room temperature. In some embodiments, the viscosity of the gel or composition which forms a gel is less than 0.1 cP at about room temperature. In some embodiments, the viscosity of the gel or composition which forms a gel is between about 0.1 cP to about 1 cP at about room temperature. In some embodiments, the viscosity of the gel or composition which forms a gel is between about 0.1 cP to about 1.5 cP at about room temperature. In some embodiments, the viscosity of the gel or composition which forms a gel is between about 0.1 cP to about 2 cP at about room temperature. In some embodiments, the viscosity of the gel or composition which forms a gel is between about 0.1 cP to about 5 cP at about room temperature. In some embodiments, the viscosity of the gel or composition which forms a gel is between about 0.1 cP to about 10 cP at about room temperature. In some embodiments, the viscosity of the gel or composition which forms a gel is between about 1 cP to about 10 cP at about room temperature. In some embodiments, the viscosity of the gel or composition which forms a gel is between about 1 cP to about 50 cP at about room temperature. In some embodiments, the viscosity of the gel or composition which forms a gel is between about 1 cP to about 100 cP at about room temperature. In some embodiments, the viscosity of the gel or composition which forms a gel is between about 100 cP to about 200 cP at about room temperature. In some embodiments, the viscosity of the gel or composition which forms a gel is between about 100 cP to about 500 cP at about room temperature. In some embodiments, the viscosity of the gel or composition which forms a gel is between about 100 cP to about 1,000 cP at about room temperature. In some embodiments, the viscosity of the gel or composition which forms a gel is between about 1,000 cP to about 2,000 cP at about room temperature. In some embodiments, the viscosity of the gel or composition which forms a gel is between about 1,000 cP to about 5,000 cP at about room temperature. In some embodiments, the viscosity of the gel or composition which forms a gel is between about 1,000 cP to about 10,000 cP at about room temperature. In some embodiments, the viscosity of the gel or composition which forms a gel is between about 10,000 cP to about 20,000 cP at about room temperature. In some embodiments, the viscosity of the gel or composition which forms a gel is between about 10,000 cP to about 50,000 cP at about room temperature. In some embodiments, the viscosity of the gel or composition which forms a gel is between about 10,000 cP to about 100,000 cP at about room temperature. In some embodiments, the viscosity of the gel or composition which forms a gel is between about 10,000 cP to about 500,000 cP at about room temperature. In some embodiments, the viscosity of the gel or composition which forms a gel is between about 100,000 cP to about 150,000 cP at about room temperature. In some embodiments, the viscosity of the gel or composition which forms a gel is between about 100,000 cP to about 200,000 cP at about room temperature. In some embodiments, the viscosity of the gel or composition which forms a gel is between about 100,000 cP to about 250,000 cP at about room temperature. In some embodiments, the viscosity of the gel or composition which forms a gel is between about 100,000 cP to about 300,000 cP at about room temperature. In some embodiments, the viscosity of the gel or composition which forms a gel is between about 100,000 cP to about 350,000 cP at about room temperature. In some embodiments, the viscosity of the gel or composition which forms a gel is between about 100,000 cP to about 400,000 cP at about room temperature. In some embodiments, the viscosity of the gel or composition which forms a gel is between about 100,000 cP to about 450,000 cP at about room temperature. In some embodiments, the viscosity of the gel or composition which forms a gel is between about 100,000 cP to about 500,000 cP at about room temperature. In some embodiments, the viscosity of the gel or composition which forms a gel is between about 200,000 cP to about 300,000 cP at about room temperature. In some embodiments, the viscosity of the gel or composition which forms a gel is between about 200,000 cP to about 400,000 cP at about room temperature. In some embodiments, the viscosity of the gel or composition which forms a gel is between about 200,000 cP to about 500,000 cP at about room temperature. In some embodiments, the viscosity of the gel or composition which forms a gel is between about 300,000 cP to about 500,000 cP at about room temperature. In some embodiments, the viscosity of the gel or composition which forms a gel is between about 400,000 cP to about 500,000 cP at about room temperature. In some embodiments, the viscosity of the gel or composition which forms a gel is between about 400,000 cP to about 600,000 cP at about room temperature.

In some embodiments the liquid component includes or consists of a gel, or a composition which forms a gel, that is configured to undergo gellation at temperatures above room temperature. In some embodiments the gel or composition which forms a gel is configured to have a gelling temperature between 25° C. and 37° C. In some embodiments the gel or composition which forms a gel is configured to be in a solid or gelled state at human body temperature (about 37° C.). In some embodiments, the viscosity of the gel or composition which forms a gel is at least 10,000 cP at about human body temperature. In some embodiments, the viscosity of the gel or composition which forms a gel is at least 20,000 cP at about human body temperature. In some embodiments, the viscosity of the gel or composition which forms a gel is at least 30,000 cP at about human body temperature. In some embodiments, the viscosity of the gel or composition which forms a gel is at least 40,000 cP at about human body temperature. In some embodiments, the viscosity of the gel or composition which forms a gel is at least 50,000 cP at about human body temperature. In some embodiments, the viscosity of the gel or composition which forms a gel is at least 60,000 cP at about human body temperature. In some embodiments, the viscosity of the gel or composition which forms a gel is at least 70,000 cP at about human body temperature. In some embodiments, the viscosity of the gel or composition which forms a gel is at least 80,000 cP at about human body temperature. In some embodiments, the viscosity of the gel or composition which forms a gel is at least 90,000 cP at about human body temperature. In some embodiments, the viscosity of the gel or composition which forms a gel is at least 100,000 cP at about human body temperature. In some embodiments, the viscosity of the gel or composition which forms a gel is at least 150,000 cP at about human body temperature. In some embodiments, the viscosity of the gel or composition which forms a gel is at least 200,000 cP at about human body temperature. In some embodiments, the viscosity of the gel or composition which forms a gel is at least 250,000 cP at about human body temperature. In some embodiments, the viscosity of the gel or composition which forms a gel is at least 300,000 cP at about human body temperature. In some embodiments, the viscosity of the gel or composition which forms a gel is at least 350,000 cP at about human body temperature. In some embodiments, the viscosity of the gel or composition which forms a gel is at least 400,000 cP at about human body temperature. In some embodiments, the viscosity of the gel or composition which forms a gel is at least 450,000 cP at about human body temperature. In some embodiments, the viscosity of the gel or composition which forms a gel is at least 500,000 cP at about human body temperature. In some embodiments, the viscosity of the gel or composition which forms a gel is at least 550,000 cP at about human body temperature. In some embodiments, the viscosity of the gel or composition which forms a gel is at least 600,000 cP at about human body temperature. In some embodiments, the viscosity of the gel or composition which forms a gel is at least 650,000 cP at about human body temperature. In some embodiments, the viscosity of the gel or composition which forms a gel is at least 700,000 cP at about human body temperature. In some embodiments, the viscosity of the gel or composition which forms a gel is at least 750,000 cP at about human body temperature. In some embodiments, the viscosity of the gel or composition which forms a gel is at least 800,000 cP at about human body temperature. In some embodiments, the viscosity of the gel or composition which forms a gel is at least 850,000 cP at about human body temperature. In some embodiments, the viscosity of the gel or composition which forms a gel is at least 900,000 cP at about human body temperature. In some embodiments, the viscosity of the gel or composition which forms a gel is at least 950,000 cP at about human body temperature. In some embodiments, the viscosity of the gel or composition which forms a gel is at least 1,000,000 cP at about human body temperature. In some embodiments, the viscosity of the gel or composition which forms a gel is between about 50,000 cP to about 100,000 cP at about human body temperature. In some embodiments, the viscosity of the gel or composition which forms a gel is between about 100,000 cP to about 200,000 cP at about human body temperature. In some embodiments, the viscosity of the gel or composition which forms a gel is between about 200,000 cP to about 300,000 cP at about human body temperature. In some embodiments, the viscosity of the gel or composition which forms a gel is between about 300,000 cP to about 400,000 cP at about human body temperature. In some embodiments, the viscosity of the gel or composition which forms a gel is between about 400,000 cP to about 500,000 cP at about human body temperature. In some embodiments, the viscosity of the gel or composition which forms a gel is between about 500,000 cP to about 600,000 cP at about human body temperature. In some embodiments, the viscosity of the gel or composition which forms a gel is between about 500,000 cP to about 700,000 cP at about human body temperature. In some embodiments, the viscosity of the gel or composition which forms a gel is between about 500,000 cP to about 800,000 cP at about human body temperature. In some embodiments, the viscosity of the gel or composition which forms a gel is between about 500,000 cP to about 900,000 cP at about human body temperature. In some embodiments, the viscosity of the gel or composition which forms a gel is between about 500,000 cP to about 1,000,000 cP at about human body temperature. In some embodiments, the viscosity of the gel or composition which forms a gel is between about 600,000 cP to about 700,000 cP at about human body temperature. In some embodiments, the viscosity of the gel or composition which forms a gel is between about 600,000 cP to about 900,000 cP at about human body temperature. In some embodiments, the viscosity of the gel or composition which forms a gel is between about 600,000 cP to about 800,000 cP at about human body temperature. In some embodiments, the viscosity of the gel or composition which forms a gel is between about 600,000 cP to about 900,000 cP at about human body temperature. In some embodiments, the viscosity of the gel or composition which forms a gel is between about 600,000 cP to about 1,000,000 cP at about human body temperature. In some embodiments, the viscosity of the gel or composition which forms a gel is between about 700,000 cP to about 800,000 cP at about human body temperature. In some embodiments, the viscosity of the gel or composition which forms a gel is between about 700,000 cP to about 900,000 cP at about human body temperature. In some embodiments, the viscosity of the gel or composition which forms a gel is between about 700,000 cP to about 1,000,000 cP at about human body temperature. In some embodiments, the viscosity of the gel or composition which forms a gel is between about 800,000 cP to about 900,000 cP at about human body temperature. In some embodiments, the viscosity of the gel or composition which forms a gel is between about 800,000 cP to about 1,000,000 cP at about human body temperature. In some embodiments, the viscosity of the gel or composition which forms a gel is between about 900,000 cP to about 1,000,000 cP at about human body temperature.

In some embodiments, the viscosity of the gel or composition which forms a gel is configured to increase at least two to three times when transitioning from about room temperature to about human body temperature. In some embodiments, the viscosity of the gel or composition which forms a gel is configured to increase at least two to four times when transitioning from about room temperature to about human body temperature. In some embodiments, the viscosity of the gel or composition which forms a gel is configured to increase at least three to four times when transitioning from about room temperature to about human body temperature. In some embodiments, the viscosity of the gel or composition which forms a gel is configured to increase at least five times when transitioning from about room temperature to about human body temperature. In some embodiments, the viscosity of the gel or composition which forms a gel is configured to increase at least ten times when transitioning from about room temperature to about human body temperature. In some embodiments, the viscosity of the gel or composition which forms a gel is configured to increase at least a hundred times when transitioning from about room temperature to about human body temperature. In some embodiments, the viscosity of the gel or composition which forms a gel is configured to increase at least a thousand times when transitioning from about room temperature to about human body temperature. In some embodiments, the increased viscosity and/or mucoadhesive properties can be advantageous by increasing the contact time of the composition with the pleura. Moreover, by having a lower viscosity when first introduced into the patient, the gel or composition which forms a gel can be more readily dispersed throughout the pleural cavity and better distributed over the surfaces of the pleura before the composition forms a gel.

The gel or composition which forms a gel according to some embodiments of the invention includes one or more polymers. In some embodiments, the gel or composition which forms a gel includes one or more synthetic polymers. In some embodiments, the gel or composition which forms a gel includes one or more tri-block copolymers. In some embodiments, the gel or composition which forms a gel includes one or more copolymers of ethylene oxide and propylene oxide. In some embodiments, the gel or composition which forms a gel includes one or more poloxamers (e.g., one or more poloxamers available under the trade names SYNPERONIC™ or PLURONICS®). In some embodiments, the gel or composition which forms a gel includes one or more polysaccharides. In some embodiments, the gel or composition which forms a gel includes xanthan gum. In some embodiments, the gel or composition which forms a gel includes a combination of one or more copolymers of ethylene oxide and propylene oxide and one or more polysaccharides. In some embodiments, the gel or composition which forms a gel includes a combination of one or more poloxamers and xanthan gum. In some embodiments, the gel or composition which forms a gel includes or consists of a combination of one or more poloxamers, xanthan gum, and water. In some embodiments, the gel or composition which forms a gel includes biocompatible monomers which are configured to polymerize after introduction into the body of the patient (e.g., into the pleural cavity) to form a biocompatible gel.

In some embodiments, the gel or composition which forms a gel includes or consists of, for example, one or more of the compositions described in U.S. Pat. Nos. 8,501,230, 8,691,278, and International Application Publication No. WO 2009/073658, all of which are incorporated herein by reference in their entireties. In some embodiments, the gel or composition which forms a gel includes or consists of, for example, TRI-726 from TRILOGIC PHARMA described in Mondal, P. et al., "Evaluation of TRI-726 as a drug delivery matrix," *Drug Development and Industrial Pharmacy,* 2011, pp 1-7, which is incorporated herein by reference in its entirety. In some embodiments, the gel or composition which forms a gel includes or consists of, for example, 10 to 25 parts by weight of one or more poloxamers, 1 to 3 parts by weight of xanthan gum, and 72 to 89 parts by weight of water. In some embodiments, the one or more poloxamers includes one or more poloxamers selected from the group consisting of Poloxamer 407 (F127), Poloxamer 338 (F108), and Poloxamer 188 (F68) available from BASF. In some embodiments, the one or more poloxamers includes or consists only of Poloxamer 407 (F127). In some embodiments, the one or more poloxamers includes or consists only of Poloxamer 338 (F108). In some embodiments, the one or more poloxamers includes or consists only of Poloxamer 188 (F68). In some embodiments, the one or more poloxamers includes or consists only of a mixture of Poloxamer 407 (F127) and Poloxamer 338 (F108). In some embodiments, the one or more poloxamers includes or consists only of a mixture of Poloxamer 407 (F127) and Poloxamer 188 (F68). In some embodiments, the one or more poloxamers includes or consists only of a mixture of Poloxamer 338 (F108) and Poloxamer 188 (F68). In some embodiments, the one or more poloxamers includes or consists only of a mixture of Poloxamer 407 (F127), Poloxamer 338 (F108) and Poloxamer 188 (F68).

When the liquid components are admixed with a gas to form a foam in accordance with certain embodiments, the resulting foam will have a substantially greater volume in comparison to the volume of the unfoamed liquid component. This increase in volume is dependent on the amount of gas which is mixed with the liquid component for form the foam. Accordingly, in some embodiments, the amount of gas that is mixed with the liquid component may be selected based on the desired volume increase. For example in some embodiments, when the liquid component is foamed, the resulting composition is configured to have a volume that is about 1 to about 1000 times greater than the volume of the unfoamed liquid component. In some embodiments, the resulting composition has a volume that is about 1 to about 2 times greater than the volume of the unfoamed liquid component. In some embodiments, the resulting composition has a volume that is about 2 to about 3 times greater than the volume of the unfoamed liquid component. In some embodiments, the resulting composition has a volume that is about 3 to about 4 times greater than the volume of the unfoamed liquid component. In some embodiments, the resulting composition has a volume that is about 4 to about 5 times greater than the volume of the unfoamed liquid component. In some embodiments, the resulting composition has a volume that is about 5 to about 6 times greater than the volume of the unfoamed liquid component. In some embodiments, the resulting composition has a volume that is about 6 to about 7 times greater than the volume of the unfoamed liquid component. In some embodiments, the resulting composition has a volume that is about 7 to about 8 times greater than the volume of the unfoamed liquid component. In some embodiments, the resulting composition has a volume that is about 8 to about 9 times greater than the volume of the unfoamed liquid component. In some embodiments, the resulting composition has a volume that is about 9 to about 10 times greater than the volume of the unfoamed liquid component. In some embodiments, the resulting composition has a volume that is about 10 to about 20 times greater than the volume of the unfoamed liquid component. In some embodiments, the resulting composition has a volume that is about 20 to about 30 times greater than the volume of the unfoamed liquid component. In some embodiments, the resulting composition has a volume that is about 30 to about 40 times greater than the volume of the unfoamed liquid component. In some embodiments, the resulting composition has a volume that is about 40 to about 50 times greater than the volume of the unfoamed liquid component. In some embodiments, the resulting composition has a volume that is about 50 to about 60 times greater than the volume of the unfoamed liquid component. In some embodiments, the resulting composition has a volume that is about 60 to about 70 times greater than the volume of the unfoamed liquid component. In some embodiments, the resulting composition has a volume that is about 70 to about 80 times greater than the volume of the unfoamed liquid component. In some embodiments, the resulting composition has a volume that is about 80 to about 90 times greater than the volume of the unfoamed liquid component. In some embodiments, the resulting composition has a volume that is about 90 to about 100 times greater than the volume of the unfoamed liquid component. In some embodiments, the resulting composition has a volume that is about 100 to about 200 times greater than the volume of the unfoamed liquid component. In some embodiments, the resulting composition has a volume that is about 200 to about 300 times greater than the volume of the unfoamed liquid component. In some embodiments, the resulting composition has a volume that is about 300 to about 400 times greater than the volume of the unfoamed liquid component. In some embodiments, the resulting composition has a volume that is about 400 to about 500 times greater than the volume of the unfoamed liquid component. In some embodiments, the resulting composition has a volume that is about 500 to about 600 times greater than the volume of the unfoamed liquid component. In some embodiments, the resulting composition has a volume that is about 600 to about 700 times greater than the volume of the unfoamed liquid component. In some embodiments, the resulting composition has a volume that is about 700 to about 800 times greater than the volume of the unfoamed liquid component. In some embodiments, the resulting composition has a volume that is about 800 to about 900 times greater than the volume of the unfoamed liquid component. In some embodiments, the resulting composition has a volume that is about 900 to about 1000 times greater than the volume of the unfoamed liquid component. In some embodiments, the resulting composition has a volume that is at least 2 times greater than the volume of the unfoamed liquid component. In some embodiments, the resulting composition has a volume that is at least 5 times greater than the volume of the unfoamed liquid component. In some embodiments, the resulting composition has a volume that is at least 10 times greater than the volume of the unfoamed liquid component. In some embodiments, the resulting composition has a volume that is at least 20 times greater than the volume of the unfoamed liquid component. In some embodiments, the resulting composition has a volume that is at least 50 times greater than the volume of the unfoamed liquid component. In some embodiments, the resulting composition has a volume that is at least 100 times greater than the volume of the unfoamed liquid component. In some embodiments, the resulting composition has a volume that is at least 200 times greater than the volume of the unfoamed liquid component. In some embodiments, the resulting composition has a volume that is at least 500 times greater than the volume of the unfoamed liquid component. In some embodiments, the resulting composition has a volume that is at least 1000 times greater than the volume of the unfoamed liquid component.

The liquid component may be admixed with the gas to form a foam using any suitable technique known in the art. In some embodiments, the liquid component is agitated (e.g., shaken, whipped, or stirred) in the presence of the gas. In some embodiments, the gas is bubbled into the liquid component using a pump or pressurized gas source. In some embodiments, the gas and the liquid component are passed through a narrow orifice, for example, the orifice of a syringe. In some embodiments, the liquid component and the gas are contained at a pressure greater than atmospheric pressure (e.g., in a pressurized can) and foams as the liquid component and gas are released into atmospheric pressure. In other embodiments, the liquid component and gas are admixed and introduced using an injector, ejector, eductor-jet pump, aspirator pump, or other device using a Venturi effect. Examples of such devices are described in U.S. Pat. Nos. 2,569,683, 5,054,688, and 6,042,089, which are each incorporated herein by reference in their entirety. In some embodiments, a predetermined amount of gas is admixed with the liquid component. Preferably the gas and liquid component are mixed until at least the desired volume of foam is produced.

In some embodiments, the foam comprises bubbles of the gas having a size range of about 0.1 mm to about 20 mm in diameter. In some embodiments, the foam comprises bubbles of the gas having a size range of about 0.5 mm to about 15 mm in diameter. In some embodiments, the foam comprises bubbles of the gas having a size range of about 1 mm to about 10 mm in diameter. In some embodiments, the foam comprises bubbles of the gas having an average diameter ranging from about 1 mm to about 20 mm. In some embodiments, the foam comprises bubbles of the gas having an average diameter ranging from about 1 mm to about 15 mm. In some embodiments, the foam comprises bubbles of the gas having an average diameter ranging from about 1 mm to about 10 mm.

In a foamed state, the compositions according to some embodiments of the present invention may provide particular advantages in treating conditions affecting the pleura or pleural cavity, for example, when used for pleurodesis. In comparison to typical chemical pleurodesis procedures, for example, foaming may improve contact between the active agent and the patient's pleura, reduce the total amount of active agent needed for pleurodesis, and/or leave less residual active agent in the patient's pleural cavity according to some embodiments. These and other advantages may result from the increase in volume caused by foaming the liquid component which, for example, allows greater distribution the one or more active agents throughout the pleural cavity. Moreover, in some embodiments, foaming may improve adherence of the composition with the pleura thereby increasing contact between the pleura and the active agent.

As described, the active agent(s) useful in the compositions of the present invention may be dissolved, dispersed, suspended, or carried by the liquid component. In some embodiments, the active agent(s) are dissolved, dispersed, suspended, or carried by the liquid component prior to foaming the liquid component. In other embodiments, the active agent(s) are added to the liquid component after the liquid component has been foamed. In some embodiments, the liquid component by itself is an active agent (e.g., capable of inducing fusion of the pleura). In some embodiments, active agents useful in embodiments of the present invention are particularly adapted for use in chemical pleurodesis. In some embodiments, the one or more active agents may be selected from any agent known in the art to be useful in chemical pleurodesis. In some embodiments, the one or more active agents includes a sclerosing agent. In some embodiments, the active agents are selected to cause irritation, inflammation, fibrosis, and/or scarring of the patient's pleura when introduced into the pleural cavity of the patient. For example, in some embodiments, the active agents include one or more agents selected from the following: doxycycline, bleomycin, tetracycline, povidone iodine, talc, silica (e.g., fumed silica), and quinacrine. In some embodiments, the active agents include a chemotherapy agent, an antibiotic, or combinations thereof. Other active agents that may be suitable for use in compositions according to embodiments of the present invention are described in U.S. Pat. No. 6,103,695, which is incorporated herein by reference in its entirety.

In some further embodiments, compositions according to the present invention include at least one active agent that is an adhesive substance configured to adhere the layers of the patient's pleura together. Preferably the adhesive substance is capable of permanently adhering the layers of the pleura together. In some embodiments, the adhesive substance includes a hemostatic sealant. In some embodiments, the adhesive substance includes a fibrin- or collagen-based tissue adhesive. In some embodiments, the adhesive substance includes one or more of fibrin sealants, gelatin-resorcin-aldehydes (e.g., gelatin-resorcin-formaldehyde/glutaraldehyde glues), protein-aldehyde systems, polysaccharide-based adhesives, mussel adhesive proteins, and biomimetic glues. In some embodiments, the adhesive substance includes one or more cyanoacrylate adhesives. The adhesive substance may be the only active agent or included in combination with other active agents, for example, an active agent configured to cause irritation, inflammation, fibrosis, and/or scarring of the patient's pleura as described above.

Compositions according to some embodiments of the present invention are not necessarily limited to use in pleurodesis. Other conditions that affect the pleura or pleural cavity of a patient may also be treated according to certain methods and compositions of the present invention. In some embodiments, for example, compositions of the present invention may be useful in administering one or more active agents for treating infections or bleeding in the pleural cavity, penumothorax, or hemothorax. According to some of these embodiments, the compositions include one or more active agents selected from antibiotics, sealants, hemostatic agents, and lytic agents. In other embodiments, the compositions include one or more agents capable of reducing fluid formation or fluid leakage into the pleural cavity. In some embodiments, the compositions include one or more agents capable of increasing fluid reabsorption. Other active agents that can be administered by methods and compositions of the present invention include cancer-treating agents, nucleotides, vaccines, biopharmaceuticals, and therapeutic proteins or polypeptides.

The one or more active agents are preferably present in the composition in a therapeutically effective amount. When used for pleurodesis, for example, the one or more active agents are preferably present in a therapeutically effective amount sufficient to cause fusion of the patient's pleura. In some embodiments, the one or more active agents are present in the composition from trace amounts to about 0.1% by weight of the liquid component. In some embodiments, the one or more active agents are present in the composition from 0.001% to about 0.1% by weight of the liquid component. In some embodiments, the one or more active agents are present in the composition from 0.01% to about 0.1% by weight of the liquid component. In some embodiments, the one or more active agents are present in the composition from 0.02% to about 0.1% by weight of the liquid component. In some embodiments, the one or more active agents are present in the composition from 0.03% to about 0.1% by weight of the liquid component. In some embodiments, the one or more active agents are present in the composition from 0.04% to about 0.1% by weight of the liquid component. In some embodiments, the one or more active agents are present in the composition from 0.05% to about 0.1% by weight of the liquid component. In some embodiments, the one or more active agents are present in the composition from 0.06% to about 0.1% by weight of the liquid component. In some embodiments, the one or more active agents are present in the composition from 0.07% to about 0.1% by weight of the liquid component. In some embodiments, the one or more active agents are present in the composition from 0.08% to about 0.1% by weight of the liquid component. In some embodiments, the one or more active agents are present in the composition from 0.09% to about 0.1% by weight of the liquid component. In some embodiments, the one or more active agents are present in the composition in an amount that is at least 0.1% by weight of the liquid component. In some embodiments, the one or more active agents are present in the composition in an amount that is at least 0.5% by weight of the liquid component. In some embodiments, the one or more active agents are present in the composition in an amount that is at least 1% by weight of the liquid component. In some embodiments, the one or more active agents are present in the composition in an amount that is at least 2% by weight of the liquid component. In some embodiments, the one or more active agents are present in the composition in an amount that is at least 5% by weight of the liquid component. In some embodiments, the one or more active agents are present in the composition in an amount that is at least 10% by weight of the liquid component. In some embodiments, the one or more active agents are present in an amount that is at least 15% by weight of the liquid component. In some embodiments, the one or more active agents are present in the composition in an amount that is at least 20% by weight of the liquid component. In some embodiments, the one or more active agents are present in the composition in an amount from about 0.1% to about 50% by weight of the liquid component. In some embodiments, the one or more active agents are present in the composition in an amount from about 0.1% to about 40% by weight of the liquid component. In some embodiments, the one or more active agents are present in the composition in an amount from about 0.1% to about 30% by weight of the liquid component. In some embodiments, the one or more active agents are present in the composition in an amount from about 0.1% to about 25% by weight of the liquid component. In some embodiments, the one or more active agents are present in the composition in an amount from about 0.1% to about 20% by weight of the liquid component. In some embodiments, the one or more active agents are present in the composition in an amount from about 0.1% to about 15% by weight of the liquid component. In some embodiments, the one or more active agents are present in the composition in an amount from about 0.1% to about 10% by weight of the liquid component. In some embodiments, the one or more active agents are present in the composition in an amount from about 0.1% to about 9% by weight of the liquid component. In some embodiments, the one or more active agents are present in the composition in an amount from about 0.1% to about 8% by weight of the liquid component. In some embodiments, the one or more active agents are present in the composition in an amount from about 0.1% to about 7% by weight of the liquid component. In some embodiments, the one or more active agents are present in the composition in an amount from about 0.1% to about 6% by weight of the liquid component. In some embodiments, the one or more active agents are present in the composition in an amount from about 0.1% to about 5% by weight of the liquid component. In some embodiments, the one or more active agents are present in the composition from about 0.1% to about 4% by weight of the liquid component. In some embodiments, the one or more active agents are present in the composition from about 0.1% to about 3% by weight of the liquid component. In some embodiments, the one or more active agents are present in the composition from about 0.1% to about 2% by weight of the liquid component. In some embodiments, the one or more active agents are present in the composition from about 0.1% to about 1% by weight of the liquid component. In some embodiments, the one or more active agents are present in the composition at less than 1% by weight of the liquid component. In other embodiments, the one or more active agents are present in the composition in an amount greater than 50% by weight of the liquid component, e.g., from 50% to 60% by weight of the liquid component, from 60% to 70% by weight of the liquid component, from 70% to 80% by weight of the liquid component, from 80% to 90% by weight of the liquid component, or from 90% to 99% by weight of the liquid component. In certain embodiments, the liquid component by itself is an active agent, for example, capable to cause irritation, inflammation, fibrosis, and/or scarring of the patient's pleura as described without the use of additional active agents. According to some of these embodiments, the amount of active agent present in the composition would be equal to the weight of the liquid component.

The compositions according to certain embodiments of the invention can be introduced into the pleural cavity of the patient using any suitable technique known in the art for introducing a fluid into the pleural cavity. In some embodiments, techniques used to introduce chemical agents during typical chemical pleurodesis procedures can also be used to introduce compositions of the present invention into the pleural cavity. In some embodiments, for example, the composition can be introduced into the pleural cavity via a catheter or chest drain that is inserted into the pleural cavity. In some embodiments, the compositions may be injected into the pleural cavity of the patient. In some embodiments, the pleural cavity is first drained or aspirated of any effusions or other fluids prior to introducing the composition. In some embodiments, the composition can be introduced during open surgery wherein the pleural cavity is directly accessible. In some of these embodiments, for example, the composition may be sprayed, poured, or otherwise directly introduced into the pleural cavity. In other embodiments, the composition can be introduced during laparoscopic, videoscopic, or robotic surgery via minimally invasive techniques.

In some embodiments, the compositions are introduced into the pleural cavity as a foam after the liquid component has been admixed with a gas. In other embodiments, the composition is introduced into the pleural cavity before the liquid component is admixed with a gas. According to these embodiments, the liquid component may then foamed within the pleural cavity by mixing the liquid component with a gas. In yet other embodiments, the liquid component is foamed as it is introduced into the pleural cavity. For example, in some embodiments, both the liquid component and a gas may be combined together as the components are introduced into the cavity. As described, for example, in some embodiments the liquid component and the gas are contained at a pressure greater than atmospheric pressure (e.g., in a pressurized can) and foams as the liquid component and gas are released into the lower pressure of the pleural cavity. In other embodiments, the liquid component and gas are admixed and introduced into the pleural cavity using an injector, ejector, eductor-jet pump, aspirator pump, or other device using a Venturi effect.

In some embodiments, the total volume of foam produced is between about 1 mL to about 100 mL. In some embodiments, the total volume of foam produced is between about 1 mL to about 10 mL. In some embodiments, the total volume of foam produced is between about 1 mL to about 2 mL, between about 2 mL to about 3 mL, between about 3 mL to about 4 mL, between about 4 mL to about 5 mL, between about 5 mL to about 6 mL, between about 6 mL to about 7 mL, between about 7 ml, to about 8 mL, between about 8 mL to about 9 mL, or between about 9 mL to about 10 mL. In some embodiments, the total volume of foam produced is between about 10 mL to about 100 mL. In some embodiments, the total volume of foam produced is between about 10 mL to about 20 mL, between about 20 mL to about 30 mL, between about 30 mL to about 40 mL, between about 40 mL to about 50 mL, between about 50 mL to about 60 mL, between about 60 mL to about 70 mL, between about 70 mL to about 80 mL, between about 80 mL to about 90 mL, or between about 90 mL to about 100 mL. In some embodiments, the total volume of foam produced is between about 50 mL to about 100 mL. In some embodiments, the total volume of foam produced is between about 75 mL to about 100 mL. In some embodiments, the total volume of foam produced is between about 100 mL to about 200 mL, between about 200 mL to about 300 mL, between about 300 mL to about 400 mL, between about 400 mL to about 500 mL, between about 500 mL to about 600 mL, between about 600 mL to about 700 mL, between about 700 mL to about 800 mL, between about 800 mL to about 900 mL, or between about 900 mL to about 1000 mL. In some embodiments, the total volume of foam produced is at least 100 mL. In some embodiments, the total volume of foam produced is at least 200 mL. In some embodiments, the total volume of the foam produced is at least 500 mL. In some embodiments, the total volume of the foam produced is at least 750 mL. In some embodiments, the total volume of the foam produced is at least 1000 mL. In some embodiments, the total volume of the foam produced is between about 500 mL to about 1000 mL. In some embodiments, the total volume of the foam produced is between about 750 mL to about 1000 mL. In some embodiments, the total volume of the foam produced is between about 1000 mL to about 1500 mL. In some embodiments, the total volume of the foam produced is between about 1500 mL to about 2000 mL.

In some embodiments, as described above, one or more active agents are dissolved, suspended, or dispersed in the liquid component prior to the liquid component being foamed. In other embodiments, the one or more active agents can be added to the foam after the liquid component has been foamed. In other embodiments, the liquid component by itself is an active agent (e.g., capable of inducing fusion of the pleura). In some embodiments, the total amount of the one or more active agents to be introduced into the pleural cavity may range from about 100 mg to about 20 g, depending on the type of active agent used. For example, when talc is used as the active agent, the total amount of talc included in the composition may range from about 1 g to about 15 g, 2 g to about 12 g, from about 2.5 g to about 10 g, from about 3 g to about 7 g, or from about 4 g to about 6 g, according to some embodiments. In other embodiments, where the active agent is doxycycline, bleomycin, tetracycline, quinacrine or combinations thereof, the total amount of active agent included in the composition may range, for example, from about 50 mg to about 2000 mg, about 100 mg to about 1000 mg, about 200 mg to about 800 mg, from about 300 mg to about 700 mg, or from about 400 mg to about 600 mg.

In certain embodiments, after the composition is introduced into the pleural cavity, the foam is allowed to contact the layers of the pleura. In some embodiments, contacting the layers of the pleura with the foam exposes the pleura to the one or more active agents that are dissolved, suspended, dispersed, and/or carried by the foam. As described above and herein, in some embodiments the foam allows greater distribution of the one or more active agents throughout the pleural cavity. For example, in some embodiments the volume of foam introduced into the pleural cavity may be sufficient to fill substantially the entire pleural cavity such that substantially all of the patient's pleura is exposed to the one or more active agents. Accordingly, certain embodiments of the present invention may avoid the problem faced during typical chemical pleurodesis procedures wherein the chemical agent collects at certain locations in the pleural cavity resulting in an uneven distribution of the chemical agent and incomplete fusion of the pleural layers. Moreover, in some embodiments, the foam may improve adherence of the composition with the pleura thereby increasing contact between the pleura and the one or more active agents.

In some embodiments particularly relating to pleurodesis, the foam is preferably allowed to contact the pleura for at least an amount of time sufficient for the active agent to initiate a reaction in or have an active effect on the layers of the pleura. In some embodiments, when used for pleurodesis for example, the foam is preferably allowed to contact the pleura for at least an amount of time sufficient for the active agent to initiate inflammation and/or adhesion of the pleural layers. In some embodiments, the desired contact time is at least 1 minute, at least 2 minutes, at least 5 minutes, at least 10 minutes, at least 15 minutes, at least 30 minutes, at least 45 minutes, or at least 60 minutes. In some embodiments, the desired contact time ranges from about 1 hour to about 24 hours, from about 2 hours to about 20 hours, from about 4 hours to about 18 hours, from about 6 hours to about 16 hours, from about 8 hours to about 14 hours, or from about 10 hours to about 12 hours.

In some embodiments, the foam may be allowed to remain within and absorbed by the patient's body. Absorption may occur over a period of one to seven days according to some embodiments. For example, in some embodiments, the foam is formulated to dissipate over time and the remaining residual liquid absorbed by the pleural layers. In other embodiments, the residual liquid or a portion thereof is drained from the patient after or while the foam dissipates. Dissipation of the foam refers to the gas escaping from the foam. In some embodiments, the foam is configured to dissipate within 1 hour, within 2 hours, within 4 hours, within 8 hours, within 12 hours, or within 24 hours. In some embodiments, the foam is configured to begin dissipation immediately after formation and/or administration to the patient. In some embodiments, the foam is configured to begin dissipation in less than a minute after formation and/or administration to the patient. In some embodiments, the foam is configured to dissipate in less than 1 hour, e.g., between 0 minutes to 60 minutes.

In other embodiments, the compositions of the present invention are actively removed from the pleural cavity after the desired amount of contact time has occurred. For example, in some embodiments, the foam introduced into the pleural cavity is removed from the pleural cavity after 5 minutes, after 30 minutes, after 1 hour, after 12 hours, after 24 hours, etc. In some embodiments, the foam is removed before 24 hours. It should be understood that removal of the composition from the pleural cavity may leave residual amounts of the composition and active agent(s) in the pleural cavity. Therefore removal of the compositions refers to removal of at least a portion of the compositions. In some embodiments, the composition may be actively removed from the patient's pleural cavity using any techniques known in the art for removing fluid from the pleural cavity. In some embodiments, removal is carried out using one or more of aspirating, draining, and intubation. In some embodiments, at least a portion of the composition is passively drained from the patient's pleural cavity by gravity. In other embodiments, at least a portion of the composition is pumped from the pleural cavity. In some embodiments, at least a portion of the foam is allowed to dissipate prior to removal from the pleural cavity. The gas released from the dissipated foam may be allowed to be absorbed by the patient's body or removed, e.g., by draining or aspirating the pleural cavity.

In certain other embodiments of the invention, the liquid component is not or may not need to be foamed in order to effectively deliver the active agent to the pleura. According to some of these embodiments, the liquid component is selected to have good adherence to the pleural layers sufficient to maintain exposure of the pleural layers to the active agent(s) that are dissolved, dispersed, suspended, or carried by the liquid component. Some such embodiments may be achieved where the liquid component includes or consists of a gel, or a composition which forms a gel (e.g., hydrogel), as described above. In some such embodiments, the gel or composition which forms a gel is not admixed with gas to form a foam. Instead, according to some these embodiments, the gel or composition which forms a gel may be introduced into the patient in a substantially liquid (low viscosity) state and allowed to form a gel within the patient without foaming. The gel or composition which forms a gel may be introduced into the patient as a liquid via a catheter, spray, injection, or other suitable technique known in the art and allowed to form a gel inside the pleural cavity. As the gel is formed, the gel contacts and adheres to the pleural layers and exposes the pleural layers to the active agent(s). The example gels or compositions which form gels described above may be used in this manner according to some embodiments of the invention. For example, the liquid component may include or consist of a combination of one or more poloxamers, xanthan gum, water, and one or more active agents. In some embodiments, the gel is configured to release the active agent over time (e.g., over a period of 1 to 10 days). Preferably the one or more active agents are mixed with the gel or composition which forms a gel prior to introduction into the patient. In some embodiments, the gel or a composition which forms a gel and the one or more active agents are introduced into the patient simultaneously. In other embodiments, the one or more active agents are introduced into the patient after the gel or a composition which forms a gel is introduced into the patient. In some embodiments, the gel is actively removed from the patient after a predetermined time. In other embodiments, the gel is configured to biodegrade and be absorbed by the patient's body. In some embodiments, the gel is configured to remain in the patient from about 1 to about 10 days. Preferably, when used for pleurodesis, the gel is configured to remain in the patient for at least a period of time sufficient for the active agent(s) to cause fusion of the pleura.

In some embodiments relating to pleurodesis, fusion of the inner and outer pleurae is achieved as a result of one or more active agents triggering fibrosis or the formation scar tissue between the inner and outer pleurae. In other embodiments, where the active agent is an adhesive substance, fusion of the pleural layers is achieved by adhering the layers together with the adhesive substance. In some embodiments, fusion of the pleural layers may occur within one to several days after treatment with the compositions of present invention. In preferred embodiments, the pleural cavity is obliterated as a result of the fusion of the pleural layers. In some embodiments, the volume of the pleural cavity is reduced to at least an extent sufficient to prevent or minimize any pleural effusions.

It should be understood that various changes, substitutions, and alterations can be made herein without departing from the spirit and scope of the invention as defined by the appended claims. It should also be apparent that individual elements identified herein as belonging to a particular embodiment may be included in other embodiments of the invention. Moreover, the scope of the present application is not intended to be limited to the particular embodiments of the process, machine, manufacture, and composition of matter, means, methods and steps described in the specification. As one of ordinary skill in the art will readily appreciate from the disclosure herein, processes, machines, manufacture, composition of matter, means, methods, or steps, presently existing or later to be developed that perform substantially the same function or achieve substantially the same result as the corresponding embodiments described herein may be utilized according to the present invention.

Furthermore, it should be understood that some of the descriptions of the present invention have been simplified to focus on elements that are relevant for a clear understanding of the invention while eliminating, for the purposes of clarity, other elements that those of ordinary skill in the art will appreciate may also comprise a portion of the invention. However, because such elements are well known in the art, and because they do not necessary facilitate a better understanding of the invention, a description of such elements is not provided herein.

What is claimed is:

1. A method for administering an active agent to a parietal pleura and/or a visceral pleura of a patient comprising:
   preparing a composition comprising a foamable liquid, a gas and the active agent;
   introducing the composition into a pleural cavity of the patient defined by the parietal pleura and the visceral pleura, wherein upon introduction, the composition forms a foam; and
   contacting the parietal pleura and/or the visceral pleura with the active agent and causing the fusion of the parietal pleura with the visceral pleura to reduce a volume of the pleural cavity,
   wherein the foam does not form a cross-linked polymer network.

2. The method of claim 1, wherein the active agent comprises one or more agents selected from the group consisting of: doxycycline, bleomycin, tetracycline, povidone iodine, talc, silica, and quinacrine.

3. The method of claim 1, wherein the active agent comprises talc.

4. The method of claim 1, wherein the foamable liquid comprises one or more copolymers of ethylene oxide and propylene oxide.

5. The method of claim 4, wherein the copolymers of ethylene oxide and propylene oxide are one or more poloxamers.

6. The method of claim 5, wherein the one or more poloxamers are selected from the group consisting of Poloxamer 407 (F127), Poloxamer 338 (F108), Poloxamer 188 (F68), and combinations thereof.

7. The method of claim 1, wherein the gas is selected from the group consisting of air, oxygen, carbon dioxide, hydrogen, helium, argon, n-butane, n-pentane, fluorocarbons, hydrofluorocarbons, and combinations thereof.

8. The method of claim 7, wherein the gas is selected from the group consisting of fluorocarbons, hydrofluorocarbons, and combinations thereof.

9. The method of claim 1, wherein the foamable liquid is an aqueous solution.

10. The method of claim 1, wherein the foam has a volume of about 10 to about 1000 times greater than the volume of the foamable liquid.

11. A method for administering talc to a parietal pleura and/or a visceral pleura of a patient comprising:
    preparing a composition comprising:
      (i) a foamable liquid comprising water and one or more copolymers of ethylene oxide and propylene oxide,
      (ii) a fluorocarbon and/or hydrofluorocarbon, and
      (iii) talc;
    introducing the composition into a pleural cavity of the patient defined by the parietal pleura and the visceral pleura, wherein upon introduction, the composition forms a foam; and
    contacting the parietal pleura and/or the visceral pleura with talc and causing the fusion of the parietal pleura with the visceral pleura to reduce a volume of the pleural cavity,
    wherein the foam does not form a cross-linked polymer network.

12. The method of claim 11, wherein the one or more copolymers of ethylene oxide and propylene oxide are one or more poloxamers.

13. The method of claim 12, wherein the one or more poloxamers are selected from the group consisting of Poloxamer 407 (F127), Poloxamer 338 (F108), Poloxamer 188 (F68), and combinations thereof.

14. The method of claim 11, wherein the foam has a volume of about 10 to about 1000 times greater than the volume of the foamable liquid.

* * * * *